United States Patent [19]
Sturm

[11] Patent Number: 5,627,372
[45] Date of Patent: May 6, 1997

[54] MEASURING ON-LINE TOBACCO ROD BASIS WEIGHT USING COMBINED HIGH ACCURACY/SLOW RESPONSE AND LOW ACCURACY/FAST RESPONSE GAUGES

[75] Inventor: Steven P. Sturm, Columbus, Ohio

[73] Assignee: ABB Industrial Systems, Inc., Columbus, Ohio

[21] Appl. No.: 576,472

[22] Filed: Dec. 21, 1995

[51] Int. Cl.[6] .................................................. G01N 23/00
[52] U.S. Cl. ........................................................ 250/308
[58] Field of Search ........................................... 250/308

[56] References Cited

U.S. PATENT DOCUMENTS

| | | | |
|---|---|---|---|
| 3,655,984 | 4/1972 | Dukes | 250/496.1 |
| 3,665,199 | 5/1972 | Cahill et al. | 250/308 |
| 4,104,522 | 8/1978 | Rees | 250/359.1 |
| 4,432,238 | 2/1984 | Tward | 73/724 |
| 4,651,755 | 3/1987 | Rudszinat | 131/84.4 |
| 4,805,641 | 2/1989 | Radzio et al. | 131/280 |
| 4,865,054 | 9/1989 | Lorenzen et al. | 131/280 |
| 5,099,118 | 3/1992 | Francis | 250/308 |
| 5,125,418 | 6/1992 | Siems | 131/84.1 |
| 5,394,097 | 2/1995 | Bechtel et al. | 324/687 |

*Primary Examiner*—Constantine Hannaher
*Attorney, Agent, or Firm*—Killworth, Gottman, Hagan & Schaeff

[57] ABSTRACT

A method and apparatus are provided for sensing basis weight of a rod of material, such as tobacco, by two basis weight sensing operations which are then combined. A first sensing operation having high accuracy but slow response time is combined with a second sensing operation having low accuracy but fast response time to result in a high accuracy and fast response time output signal. The first sensing operation is performed using a low radiation beta gauge which does not require licensing or safety precautions required by currently used beta gauges. The second sensing operation is performed using a dielectric sensor. The output signals from the first and second sensing operations are time averaged and combined such that the fast response output signals from the second sensing operation are calibrated or biased using the output signals from the first sensing operation to result in a high accuracy and fast response time measurement of the basis weight for a rod of material, such as tobacco.

19 Claims, 2 Drawing Sheets

MEASURING ON-LINE TOBACCO ROD BASIS WEIGHT USING COMBINED HIGH ACCURACY/SLOW RESPONSE AND LOW ACCURACY/FAST RESPONSE GAUGES

BACKGROUND OF THE INVENTION

The present invention relates in general to the measurement of products produced in the tobacco industry and, more particularly, to a method and apparatus for performing on-line measurements of the basis weight of rods of material produced in the tobacco industry by means of a high accuracy, slow response, gauge in combination with a low accuracy, fast response gauge. It is currently preferred to use a low level beta gauge as the high accuracy, slow response gauge and a dielectric sensor as the low accuracy, fast response gauge and, accordingly, the invention will be described herein with primary reference to these preferred gauges.

A beta gauge is commonly used for on-line measurement of rods of material, such as tobacco, in the tobacco industry. One such beta gauge uses a 25 millicurie Strontium 90 radiation source on one side of the rod and an ionization chamber on the opposite side of the rod. Unfortunately, this beta gauge and other known beta gauges require licensing by appropriate nuclear regulatory agencies which impose a number of safety restrictions including, for example, operator training and qualification of safety officers. These regulations make the instruments difficult to ship between factories and countries and also entail high costs of training and maintaining safety officers. In addition, whether real or perceived, there is often a concern over safety and health risks related to regulated nuclear gauging equipment.

In view of these problems with existing gauging devices, there has been an attempt to eliminate nuclear gauging equipment from devices used to measure basis weight in products produced by the tobacco industry. One example is illustrated in U.S. Pat. No. 5,125,418 wherein fibrous material, such as tobacco, is monitored using an optical monitor to determine the mass flow of the solid part of the material. Also the liquid part of the material is monitored by passing the material through a high frequency electric field. Signals representative of the solid part of the material and the liquid part of the material are combined to generate a signal representative of the combined mass flow of the solid and liquid parts which is used to control the basis weight of the material flow. Unfortunately, there are problems associated with this device and it is applicant's understanding that it has not met with commercial success.

Accordingly, there is a need for an improved arrangement for measuring basis weight in rods of material, such as tobacco, produced by the tobacco industry which does not require licensing by nuclear regulatory agencies.

SUMMARY OF THE INVENTION

This need is met by the invention of the present application wherein a method and apparatus are provided for sensing basis weight of a rod of material, such as tobacco, by two basis weight sensing operations which are then combined. A first sensing operation having high accuracy but slow response time is combined with a second sensing operation having low accuracy but fast response time to result in a high accuracy and fast response time output signal. As illustrated, the first sensing operation is performed using a low radiation beta gauge which does not require licensing or safety precautions required by currently used beta gauges. The second sensing operation is illustrated as being performed using a dielectric sensor. The output signals from the first and second sensing operations are time averaged and combined such that the fast response output signals from the second sensing operation are calibrated or biased using the output signals from the first sensing operation to result in a high accuracy and fast response time measurement of the basis weight for a rod of material, such as tobacco. While a low radiation beta gauge and a dielectric sensor are currently preferred, other devices can be used in the invention of the present application.

In accordance with one aspect of the present invention, a method for on-line determination of basis weight of a rod of material comprises the steps of: measuring basis weight of a rod of material with a high accuracy first sensing device having a slow response time; measuring basis weight of the rod of material with a low accuracy second sensing device having a fast response time; and, calibrating the second sensing device using the first sensing device to obtain a fast response high accuracy signal.

In accordance with a second aspect of the present invention, a method for on-line determination of basis weight of a rod of material comprises the steps of: monitoring basis weight of a rod of material with a high accuracy first sensing device having a slow response time; maintaining a running average of basis weight determined by the first sensing device; monitoring basis weight of the rod of material with a low accuracy second sensing device having a fast response time; maintaining a running average of basis weight determined by the second sensing device; calculating a correction factor for the second sensing device based on the running averages; and, applying the correction factor to the second sensing device to generate a fast response, high accuracy basis weight for the rod of material. Preferably, the step of measuring basis weight of a rod of material with a high accuracy first sensing device comprises the step of measuring the basis weight of the rod of material with a low radiation beta gauge; and the step of measuring basis weight of the rod of material with a low accuracy second sensing device comprises the step of measuring the basis weight of the rod of material with a dielectric sensor. The method may further comprise the step of using Ruthenium 106 as a radiation source and limiting the radiation source to a maximum of 1.0 microcurie.

In accordance with yet another aspect of the present invention, apparatus for on-line determination of basis weight of a rod of material comprises a low radiation beta gauge for generating a high accuracy, high response time basis weight signal, and a dielectric sensor for generating a low accuracy, low response time basis weight signal. A processor provides for combining the high accuracy, high response time basis weight signal and the low accuracy, low response time basis weight signal to generate a high accuracy, low response time basis weight signal.

The low radiation beta gauge may comprise a radiation source of Ruthenium 106 having a maximum of 1.0 microcurie positioned on a first side of a rod of material, and a Geiger-Muller tube positioned on a second side of the rod of material opposite to the first side, the tube being positioned to receive radiation from the radiation source. The dielectric sensor may comprise open air first and second capacitors sized to receive a rod of material whose basis weight is to be determined, and circuitry connected to the first and second capacitors for determining the difference between the dielectric material within the first and second capacitors.

The circuitry may comprise a four-arm bridge circuit with the first and second capacitors forming first and second arms of the bridge circuit. The bridge circuit may be driven by an ac source having a frequency of approximately 100 megahertz. The apparatus may further comprise a peak detector for demodulating an output of the bridge circuit. The first and second capacitors each may comprise at least two capacitor plates with the illustrated first and second capacitors each comprising two arcuate capacitor plates.

It is, thus, an object of the present invention to provide an improved method and apparatus for measuring basis weight in rods of material, such as tobacco, which does not require licensing by nuclear regulatory agencies; to provide an improved method and apparatus for measuring basis weight in rods of material by means of a first sensing operation having high accuracy but slow response time which is combined with a second sensing operation having low accuracy but fast response time to result in a high accuracy and fast response time output signal; and, to provide an improved method and apparatus for measuring basis weight in rods of material by the combination of a low radiation beta gauge which does not require licensing or safety precautions required by currently used beta gauges and a dielectric sensor.

Other objects and advantages of the invention will be apparent from the following description, the accompanying drawings and the appended claims.

DETAILED DESCRIPTION OF THE INVENTION

Figure 1:
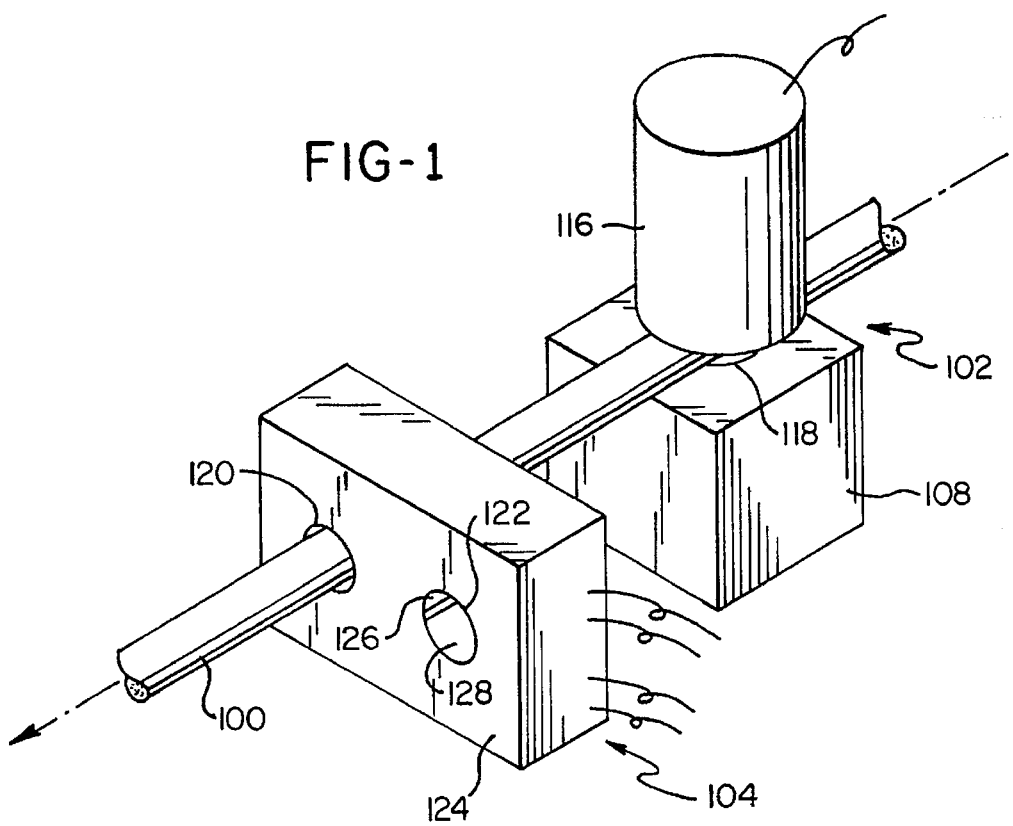
FIG. 1 is a schematic perspective view of a low radiation beta gauge and a dielectric sensor illustrative of use in accordance with the present invention for on-line measurement of basis weight of a rod of material produced by the tobacco industry.

The present invention now will be described with reference to the drawing figures wherein FIG. 1 schematically illustrates a rod of material produced by the tobacco industry, for example a tobacco rod 100, passing through a high accuracy, slow response first sensing device 102 and a low accuracy, fast response second sensing device 104, both of which measure basis weight of the rod 100. In accordance with the invention of the present application, an output signal from the slow response first sensing device 102, which over time produces a very accurate output signal representative of basis weight of the rod 100, is combined with the output signal from the fast response second sensing device 104 to produce a high accuracy output signal having a fast response which is representative of basis weight of the rod 100.

It is currently preferred to use a low level beta gauge as the high accuracy, slow response first sensing device 102 and a dielectric sensor as the low accuracy, fast response second sensing device 104 and, accordingly, the invention will be described herein with primary reference to these preferred devices. However, it is to be understood that other devices can be used in the present invention for the high accuracy, slow response first sensing device 102 and the low accuracy, fast response second sensing device 104.

For example, the dielectric sensor can be replaced by a sensor operating at mid or far infrared wavelengths or by a small machine generated X-ray sensor, while the low level beta gauge can be replaced by a mass balance technique wherein tobacco weight flow is accurately measured and correlated to average rod weight using measurements of the rod dimension and velocity. Other sensors will surely be suggested to those skilled in the art from a review of the present disclosure. Further, while the invention will be described with reference to measurement of a tobacco rod, it is to be understood that the invention is generally applicable not only to rods of material other than tobacco produced by the tobacco industry but also to other industries which face similar measurement and control requirements.

In the illustrative embodiment, the first sensing device 102 comprises a low radiation beta gauge having a housing 108 which contains a radiation source 110. The radiation source 110 is made up of source rod 112 having a small disc of Ruthenium 106 (Ru 106) isotope 114 at its distal end. While Ru 106 is the currently preferred radiation source, other sources, such as Cerium 144 (Ce 144) and monoenergetic electron emitters such as Bismuth 207 (Bi 207) can also be used. The radiation source 110 is limited to a maximum of 1.0 microcurie (37 kiloBecquerel (kBq)) such that it does not require licensing by nuclear regulatory agencies. The United States Nuclear Regulatory Commission (USNRC) in regulation §§ 30.18 and 30.71 Schedule B define that 1.0 microcurie is the maximum exempt quantity of Ru 106 while proposed European Union exempt quantities for Ru 106 is 2.7 microcuries (100 kBq). Accordingly, the first sensing device 102 does not require licensing, radiological training and safety officers.

Figure 2:
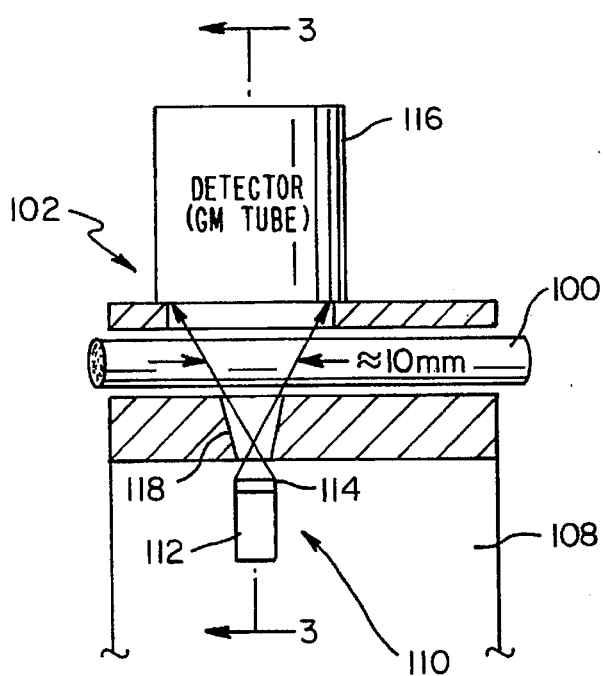
FIG. 2 is a schematic sectional view through the center of the low radiation beta gauge of FIG. 1.
Figure 3:
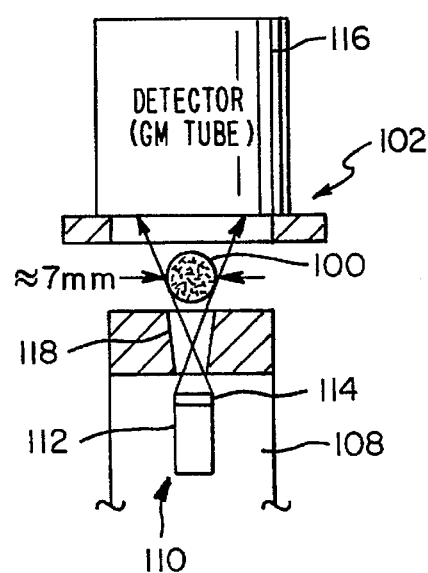
FIG. 3 is a schematic sectional view of the low radiation beta gauge taken along the section line 3—3 of FIG. 2.

As shown in FIGS. 1-3, the housing 108 containing the radiation source 110 is placed on one side of the rod 100. A radiation detector 116 is associated with the radiation source 110 substantially diametrically opposite the radiation source 110. As illustrated and currently preferred, the radiation detector 116 comprises a Geiger-Muller tube optimized to detect beta particles in the energy range of 1 to 3 MeV. Since basic measurement physics of the low radiation of the illustrated first sensing device 102 are nearly the same as currently available higher radiation beta gauges, the first sensing device 102 or low radiation beta gauge has good accuracy and reproducibility when its output signals are averaged over time. As shown in FIGS. 3 and 2, respectively, substantially the entire cross section of approximately 7 mm of the rod 100 is scanned along a length of approximately 10 mm via a generally elliptical aperture 118 through the housing 108.

Figure 5:
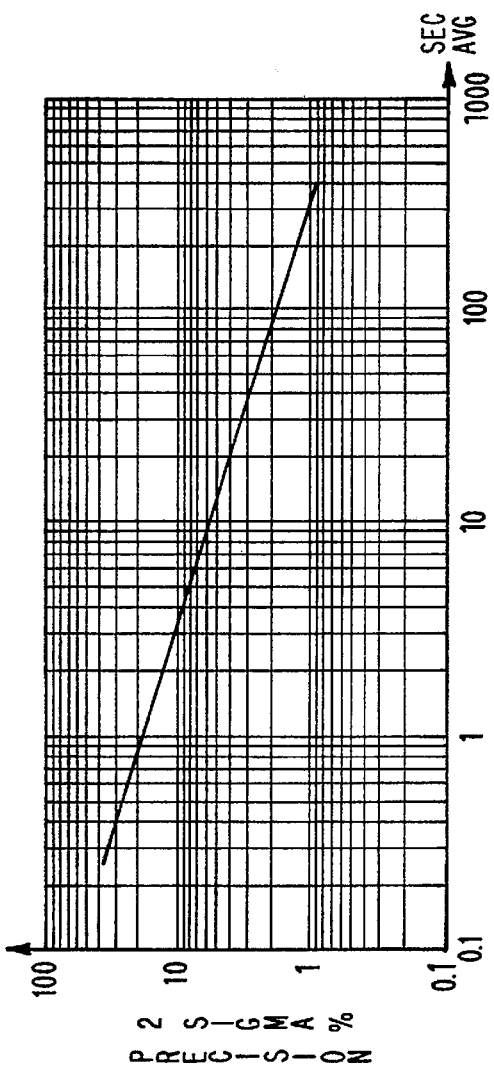
FIG. 5 is a graph of estimated precision over time for the low radiation beta gauge of FIGS. 1-3 with a radiation source of 1.0 microcurie of Ruthenium 106 (Ru 106).

Since the signal to noise ratio is poor in the low radiation beta gauge, long averaging times are required thus making its response time slow. FIG. 5 is an estimate, based on Poisson statistics and geometry factors, for precision of the low radiation beta gauge using Ru 106 (1.0 microcurie). Geometry factors include the solid angle between the isotropic radiation field and the detector 116, acceptance aperture of the detector 116 and the attenuation of windows between the radiation source 110 and the detector 116. As shown in FIG. 5, the first sensing device 102 or low radiation beta gauge is estimated to have a precision of ±6% of basis weight of the rod 100 in approximately 10 seconds with the precision reaching approximately ±1.7% precision in about two minutes.

Figure 4:
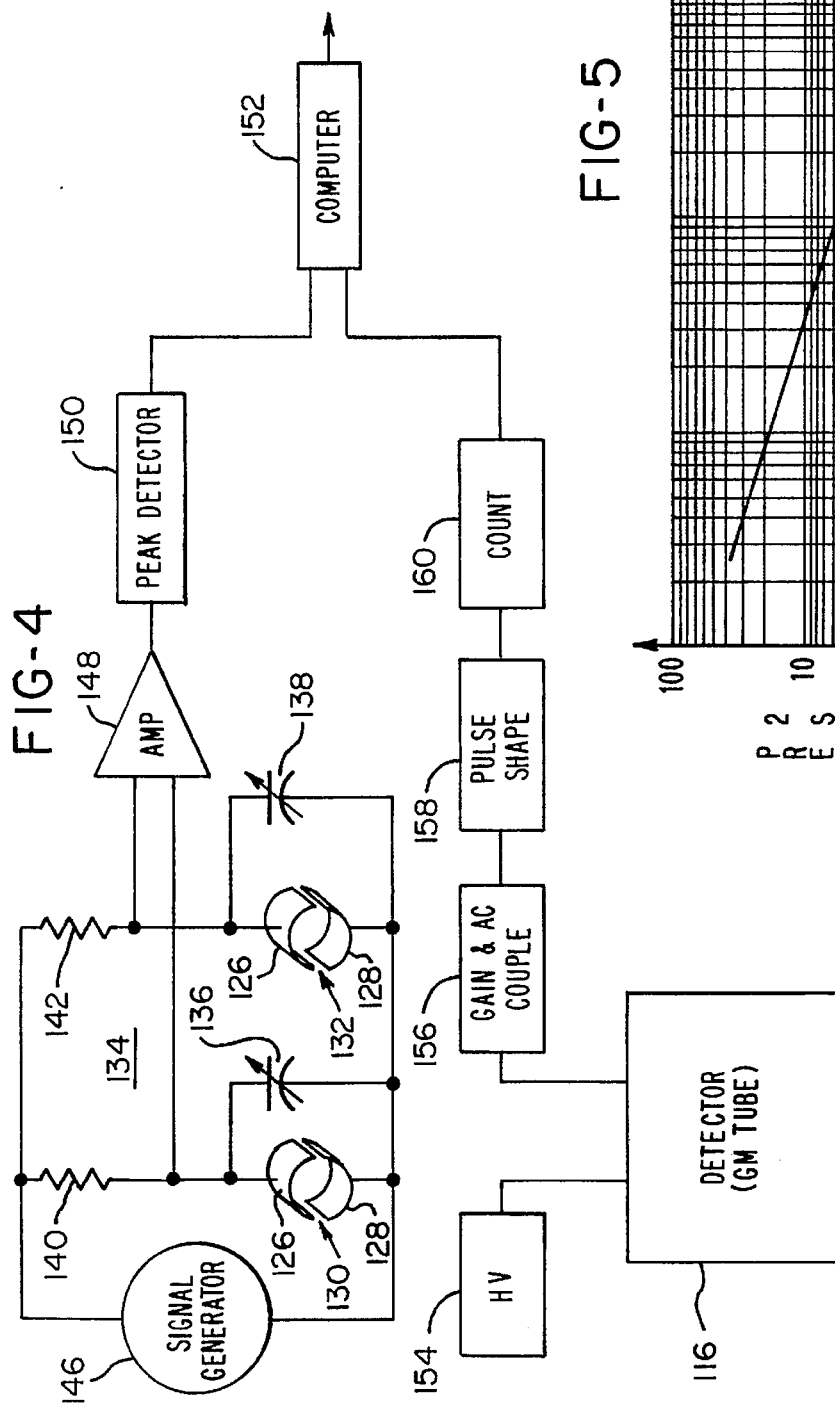
FIG. 4 is a schematic block diagram of an illustrative system in accordance with the present invention for measuring basis weight of a rod of material produced by the tobacco industry.

In the illustrative embodiment, the second sensing device 104 comprises a dielectric measurement of the rod 100 using a balance bridge or differential capacitance sensing arrangement. As illustrated in FIG. 1, a first hole 120 and a second hole 122 are formed through a block 124 of insulating material with the rod 100 passing through the first hole 120. The first and second holes 120, 122 are just large enough for the rod 100 to pass therethrough. A Bernoulli effect air film may be formed inside the first hole 120 to assist in guiding and controlling the rod 100 as it passes through the first hole 120. Inside each of the first and second holes 120, 122 are electrodes 126, 128 which form plates of capacitors 130, 132 as shown in FIG. 4. In a working embodiment, the electrodes 126, 128 extend approximately 10 mm in the axial direction of the rod 100, i.e., the machine direction for the machine (not shown) producing the rod 100.

It is noted that the geometry of the electrodes 126, 128 is not restricted to the illustrated two electrode arcuate structure but can be constructed using many electrodes around the inner circumference of the first and second holes 120, 122. It is also noted that flat rather than arcuate electrodes may be used with the holes then forming an appropriate geometric form.

Construction of the second sensing device 104 using many electrodes and/or flat electrodes should be optimized to reduce position sensitivity of the rod 100 within the first hole 120 and sensitivity due to the separation of the electrodes. Thus, if many electrodes are used, the capacitors 130, 132 are formed by parallel combinations of the electrodes having positive and negative plates positioned alternately around the circumference or peripheral boundary of the first and second holes 120, 122.

The capacitors 130, 132 are connected into two legs of a bridge circuit 134. Variable capacitors 136, 138 are used to balance the bridge 134 before the rod 100 is passed through the first hole 120. In a working embodiment of the present invention, the variable capacitors 136, 138 were formed from small pieces of wire. The other two legs of the bridge circuit 134 comprise resistors 140, 142.

The bridge circuit 134 is driven by a signal generator 146 which, in a working embodiment, was operated at a frequency of approximately 100 megahertz (Mhz). When the rod 100 is passing through the first hole 120 in the block 124 between the electrodes 126, 128 located within the first hole 120, the bridge circuit 134 is imbalanced thus generating an output signal having a frequency of approximately 100 Mhz across the bridge circuit 134. In the case of a tobacco rod, such as the tobacco rod 100, the primary constituent influencing the dielectric constant is water and provides excellent correlation to basis weight provided percent moisture of the tobacco is constant over short time periods.

The output signal from the bridge circuit 134 is amplified by an amplifier 148 and demodulated to have a fast response time. As illustrated, demodulation is performed by a peak detector 150; however, demodulation can be performed in other ways including, for example, rectification and synchronous demodulation. In any event, the demodulated signal from the bridge circuit 134 is passed to a signal processing computer 152.

The detector 116 of the low radiation first sensing device 102 is shown in FIG. 4 together with conventional associated circuitry blocks. The detector 116 is biased by a high voltage source 154 with output signals from the detector 116 passing through gain and AC coupling circuitry 156. The output signals from the detector 116 then pass through pulse shaping circuitry 158 and counter circuitry 160 before passing to signal processing computer 152.

The signal processing computer 152 samples signals originating from both the first sensing device 102 and the second sensing device 104, and forms a running average of each signal. The time period of the running average can be selected depending upon the accuracy requirements of the user. The two time averaged signals are used to derive a value to bias or calibrate the output signal of the second sensing device 104 to make its running average agree with the running average of the first sensing device 102.

One possible signal processing arrangement will now be described. The output signal D1 of the first sensing device 102 is transformed by a function of D1, f(D1). The function of D1, f(D1), is a nonlinear transformation of counts into basis weight and is very similar to transformations used in beta gauges which are currently used for measuring rods of material produced in the tobacco industry.

$$f(D1) = t_1/(A_1 + B_1 \cdot t_1 + C_1 \cdot t_1^2 + D_1 \cdot t_1^3) = w + t_o$$

$$t_1 = -ln(D1/AirCnt)$$

$$AirCnt = I0_1 \cdot e^{-T \cdot ln(2)/HL}$$

where: D1 is the output signal of the first sensing device 102, i.e., the count rate of the measured radiation sample; $A_1$–$D_1$ are sensor calibration constants; $I0_1$ is the count rate without a sample present, i.e., a standardization signal; HL is the half-life of the radiation source, a universal constant; T is the time since the last empty gap or standardization reading was performed; w is the weight of water; and, $t_o$ is the weight of material in the rod, such as tobacco. Beta gauges have approximately equal sensitivity to water and tobacco.

The output signal D2 of the second sensing device 104 is an analog signal which increases as the dielectric constant of the measured material increases. The output signal D2 of the second sensing device 104 is transformed by a function of D2, f(D2), which can be characterized by the equation:

$$f(D2) = A_2 \cdot t_2 + B_2 \cdot t_2^2 + C_2 \cdot t_2 \cdot RodT = w + \delta t_o$$

$$t_2 = (D2 - I0_2) \cdot Iosc/Ical$$

where: D2 is the output signal of the second sensing device 104; $I0_2$ is the amplitude of the bridge signal with no sample present, i.e., a standardization signal; Iosc is the amplitude of the of the output signal of the signal generator 146; Ical is the amplitude of the output signal of the signal generator 146 at calibration, a constant; $A_2$–$C_2$ are sensor calibration constants; RodT is a measured rod temperature minus a calibration temperature; $\delta$ is the partial response to material in the rod, such as tobacco; w is the weight of water; and, $t_o$ is the weight of material in the rod, such as tobacco.

The signal D2 is first corrected ($t_2$) for any slight imbalance in the bridge circuit 134 and drift in the amplitude of the output signal from the signal generator 146. Constants $A_2$ and $B_2$ linearize and scale voltage to units that correlate to water weight, for example, mg/cm of rod water weight. The constant $C_2$ scales temperature correction and operates like a slope change to the signal as determined by conditioning the moisture in the rod over the 5 to 25 percent moisture range. After the moisture calibration, the rod is dried and measured at 0% moisture. A value for $\delta$ is determined which represents the relative moisture sensitivity to the material, such as tobacco. For example, if a dry tobacco rod weight is 95 mg/cm and the calibrated sensor indicates an effective water weight of 19 mg/cm, then $\delta=0.2$ (19÷95).

For tobacco, the partial response is larger than would be expected, δ=0.044, from the ratio of dielectric constants of water, 78, versus tobacco, 3.5. This discrepancy is because a large fraction of the water in the tobacco is bound to the tobacco cellulose by hydrogen bonding. The tightly bound water is not free to rotate or align in the applied field reducing its effect as a dielectric. A more reasonable estimate for δ for tobacco is approximately 0.2 which is a calibration constant for processing signals from the second sensing device 104.

The running averages of the output signals from the first sensing device 102 and the second sensing device 104 are used to calculate an intermediate comparison value, M, of the output signals from the first and second sensing devices 102, 104 which is then used to calculate a calibration value or correction factor, a, for the output of the second sensing device 104 by solving the following equations:

$$M=((\overline{f(D1)}/\overline{f(D2)})-\delta)/(1+\overline{f(D1)}/\overline{f(D2)})$$

$$a=(M+1)/(M+\delta)$$

where the bars indicate that the running averages of f(D1) and f(D2) are used in the equation.

The calibration value, a, or correction factor is then used as a multiplier for the output signal from the second sensing device 104 to force the running average of the output signals from the second sensing device 104 to agree with the running average of the first sensing device 102. Thus, an accurate, reproducible, fast response output signal having a good signal to noise ratio is produced to represent the basis weight of the rod of material being produced. This final calculation is preformed by the following equation:

$$a \cdot f(D2) = w + t_o$$

Since some time is required for the basis weight measuring system of FIG. 4 to provide accurate readings upon initial operation, the system must be precalibrated. Precalibration can be performed based on past operation of the basis weight measuring system and the rod production equipment with which it is associated. It is also possible to precalibrate the basis weight measuring system to a value which will assure satisfactory but not ideal product. That is, precalibration can be set to ensure that the basis weight of material contained in the rod is at least equal to a minimum value even though it may be substantially higher during the initialization process.

Having thus described the invention of the present application in detail and by reference to preferred embodiments thereof, it will be apparent that modifications and variations are possible without departing from the scope of the invention defined in the appended claims.

What is claimed is:

1. A method for on-line determination of basis weight of a rod of material comprising the steps of:

measuring basis weight of a rod of material with a high accuracy low radiation beta gauge having a slow response time;

measuring basis weight of said rod of material with a low accuracy dielectric sensor having a fast response time; and calibrating said dielectric sensor using said low radiation beta gauge to obtain a fast response high accuracy signal.

2. A method for on-line determination of basis weight of a rod of material as claimed in claim 1 further comprising the step of using Ruthenium 106 as a radiation source.

3. A method for on-line determination of basis weight of a rod of material as claimed in claim 2 further comprising the step of limiting said radiation source to a maximum of 1.0 microcurie.

4. A method for on-line determination of basis weight of a rod of material as claimed in claim 1 further comprising the step of forming said dielectric sensor by performing the steps of:

forming first and second open air capacitors sized substantially the same as one another and to receive a rod of material whose basis weight is to be determined through one of said first and second open air capacitors; and connecting said first and second open air capacitors to circuitry to determine the difference between the dielectric materials within said first and second capacitors.

5. A method for on-line determination of basis weight of a rod of material comprising the steps of:

monitoring basis weight of a rod of material with a high accuracy low radiation beta gauge having a slow response time;

maintaining a running average of basis weight determined by said low radiation beta gauge;

monitoring basis weight of said rod of material with a low accuracy dielectric sensor having a fast response time;

maintaining a running average of basis weight determined by said dielectric sensor;

calculating a correction factor for said dielectric sensor based on said running averages; and applying said correction factor to said dielectric sensor to generate a fast response, high accuracy basis weight for said rod of material.

6. A method for on-line determination of basis weight of a rod of material as claimed in claim 5 further comprising the step of using Ruthenium 106 as a radiation source.

7. A method for on-line determination of basis weight of a rod of material as claimed in claim 6 further comprising the step of limiting said radiation source to a maximum of 1.0 microcurie.

8. A method for on-line determination of basis weight of a rod of material as claimed in claim 7 wherein said material is tobacco.

9. A method for on-line determination of basis weight of a rod of material as claimed in claim 5 further comprising the step of forming said dielectric sensor by performing the steps of:

forming first and second open air capacitors sized substantially the same as one another and to receive a rod of material whose basis weight is to be determined through one of said first and second open air capacitors; and connecting said first and second open air capacitors to circuitry to determine the difference between the dielectric materials within said first and second capacitors.

10. Apparatus for on-line determination of basis weight of a rod of material comprising:

a low radiation beta gauge for generating a high accuracy, high response time basis weight signal;

a dielectric sensor for generating a low accuracy, low response time basis weight signal; and a processor for combining said high accuracy, high response time basis weight signal and said low accuracy, low response time basis weight signal to generate a high accuracy, low response time basis weight signal.

11. Apparatus for on-line determination of basis weight of a rod of material as claimed in claim 10 wherein said low radiation beta gauge comprises:

a radiation source of Ruthenium 106 having a maximum of 1.0 microcurie positioned on a first side of a rod of material; and a Geiger-Muller tube positioned on a second side of said rod of material opposite to said first side, said tube being positioned to receive radiation from said radiation source.

12. Apparatus for on-line determination of basis weight of a rod of material as claimed in claim 11 wherein said dielectric sensor comprises:

open air first and second capacitors sized to receive a rod of material whose basis weight is to be determined; and circuitry connected to said first and second capacitors for determining the difference between the dielectric materials within said first and second capacitors.

13. Apparatus for on-line determination of basis weight of a rod of material as claimed in claim 12 wherein said circuitry comprises a four-arm bridge circuit with said first and second capacitors forming first and second arms of said bridge circuit.

14. Apparatus for on-line determination of basis weight of a rod of material as claimed in claim 13 wherein said bridge circuit is driven by an ac source having a frequency of approximately 100 megahertz.

15. Apparatus for on-line determination of basis weight of a rod of material as claimed in claim 14 further comprising a peak detector for demodulating an output of said bridge circuit.

16. Apparatus for on-line determination of basis weight of a rod of material as claimed in claim 12 wherein said first and second capacitors each comprise at least two capacitor plates with inter-relating pairs of said at least two capacitor plates being mounted on generally opposite sides of said first and second open air capacitors.

17. Apparatus for on-line determination of basis weight of a rod of material as claimed in claim 16 wherein said first and second capacitors each comprise two arcuate capacitor plates mounted on generally opposite sides of said first and second open air capacitors.

18. Apparatus for on-line determination of basis weight of a rod of material as claimed in claim 17 wherein said material is tobacco.

19. Apparatus for on-line determination of basis weight of a rod of material as claimed in claim 12 wherein said open air first and second capacitors are sized substantially the same as one another and to receive a rod of material whose basis weight is to be determined through one of the first and second open air capacitors.

* * * * *